United States Patent [19]
Sjøholm et al.

[11] Patent Number: 5,882,906
[45] Date of Patent: Mar. 16, 1999

[54] STAPHYLOTHERMUS AMYLASE

[75] Inventors: Carsten Sjøholm, Bagsværd, Denmark; Garabed Antranikian, Hamburg-Harburg, Germany

[73] Assignee: Novo Nordisk A/S, Bagsvaerd, Denmark

[21] Appl. No.: 765,123

[22] PCT Filed: Mar. 2, 1995

[86] PCT No.: PCT/DK95/00096

§ 371 Date: Sep. 9, 1996

§ 102(e) Date: Sep. 9, 1996

[87] PCT Pub. No.: WO95/23851

PCT Pub. Date: Sep. 8, 1995

[30] Foreign Application Priority Data

Mar. 4, 1994 [DK] Denmark ................................. 257/94

[51] Int. Cl.⁶ ............................... C12P 7/06; C12N 9/28; C12N 1/12; C13K 1/06
[52] U.S. Cl. ...................... 435/161; 435/202; 435/252.1; 127/38
[58] Field of Search ................... 435/252.1, 161, 435/202; 127/38

[56] References Cited

U.S. PATENT DOCUMENTS

| | | | |
|---|---|---|---|
| 4,284,722 | 8/1981 | Tamuri et al. | 435/94 |
| 4,810,647 | 3/1989 | Monceaux et al. | 435/106 |
| 5,059,430 | 10/1991 | Bowles | 426/20 |
| 5,370,997 | 12/1994 | Antranikian et al. | 435/71.2 |

FOREIGN PATENT DOCUMENTS

WO 91/19791  12/1991  WIPO .

OTHER PUBLICATIONS

Canganella et al. "characterization of amylolytic and pullylytic enzymes from thermophilic archaea and from a new Fervidobacterium species", Appl. Microbiol. Biotech. (1994) 42:239–245.
Brown et al., "Characterization of Amylolytic Enzyme Activities Associated With The Hyperthermophilic Archaebacterium *Pyrococcus furiosus*", Applied And Environmental Microbiology, Jul. 1990, pp. 1985–1991. vol. 56 No. 7.
Koch et al., "Purification And Properties Of A Hyperthermoactive α–amylase From The Archaeobacterium *Pyrococcus woesei*", Arch Microbiol. 1991, vol. 155 : pp. 572–578.
Saha et al., "Novel Highly Thermostable Pullulanase From Thermophiles", Tibech–Sep. 1989, vol. 7, pp. 234–238.
Abstract–Dialog—Med. 92—Dialog Accession No. 94079331.
Abstract–Dialog—File:55 Biosis No. 98091261.

*Primary Examiner*—Jon P. Weber
*Assistant Examiner*—Susan Hanley
*Attorney, Agent, or Firm*—Steve T. Zelson, Esq.; Valeta Gregg, Esq.

[57] ABSTRACT

The present invention relates to an amylase isolated from *Staphalothermus marinus*, DSM 3639, having a temperature optima of 95°–105° C., determined at pH 5.5 and a pH optima of 4.5 to 5.5, determined at 95° C. The amylase can be employed in the production of sweeteners and ethanol.

6 Claims, 2 Drawing Sheets

STAPHYLOTHERMUS AMYLASE

CROSS-REFERENCE TO RELATED APPLICATIONS

This application is a 35 U.S.C. 371 national application of PCT/DK95/00096 filed 2 Mar., 1995, the text of which is incorporated herein by reference.

FIELD OF INVENTION

The present invention relates to a novel thermostable amylase and its use in the production of sweeteners and ethanol from starch.

BACKGROUND OF THE INVENTION

The production of sweeteners from starch has been largely improved by application of different microbial enzymes to obtain better quality and yields, but the necessity of performing several steps of the starch-hydrolysing process at elevated temperatures means that there is still a need for new starch-hydrolysing enzymes with increased thermal stability.

It is known that Pyrococcus, e.g. *Pyrococcus wosei* and *Pyrococcus furiosus*, for reference see *Arch. Microbiol.* 155, 1991, pp. 572–578, and *Appl. Env. Microbiol.* 56, 1990, pp. 1985–1991, can produce highly thermostable amylases.

It is the object of this invention to provide an amylase with temperature optimum at 80° C. or above 80° C.

SUMMARY OF THE INVENTION

We have unexpectedly found that a novel thermostable amylase can be obtained from the genus Staphylothermus, a genus not previously reported to produce thermostable amylase; this new enzyme has temperature optimum around 100° C.

Accordingly, the invention provides an amylase preparation, characterized by being produced by cultivation of an amylase producing strain of the genus Staphylothermus.

BRIEF DESCRIPTION OF DRAWINGS

The present invention is further illustrated by reference to the accompanying drawings, in which.

DETAILED DISCLOSURE OF THE INVENTION

The Microorganism

Figure 1:
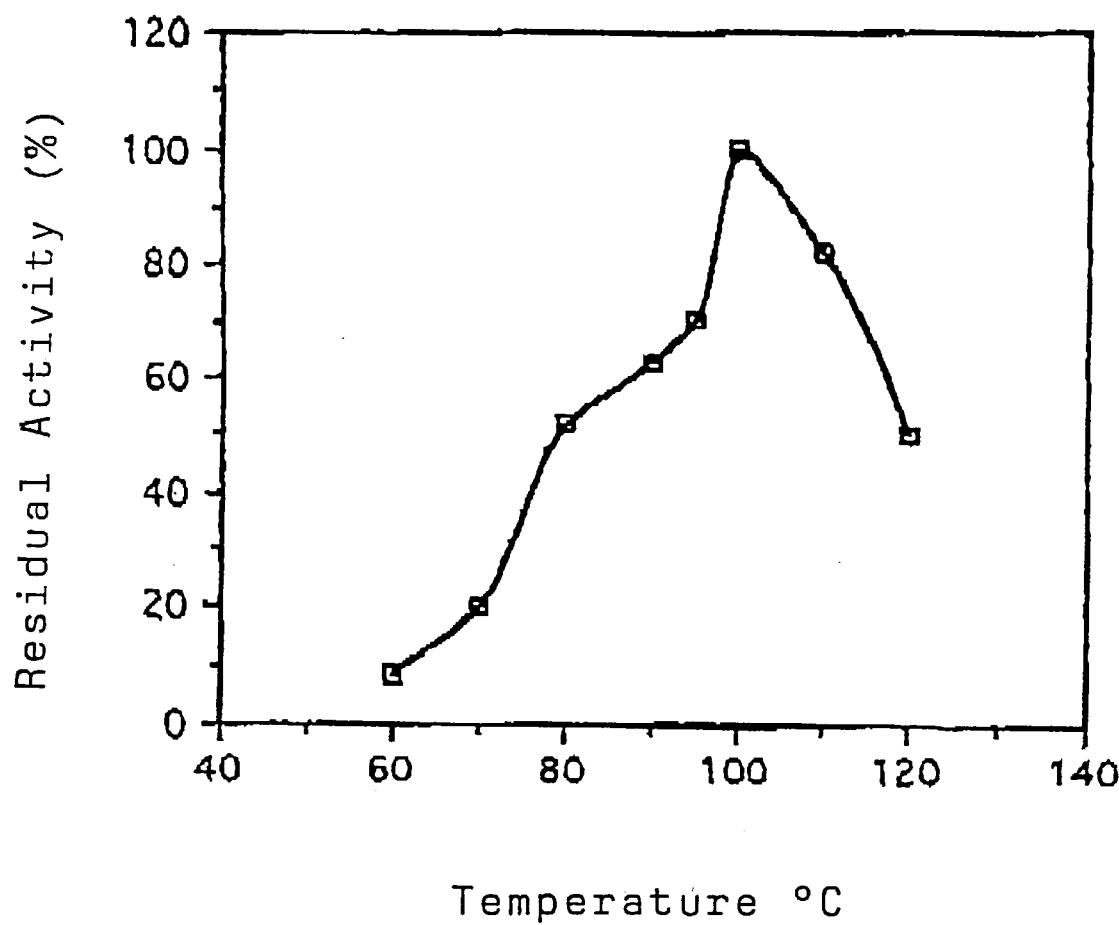
FIG. 1 shows the relative activity (% rel.) of an amylase ($\bowtie$) of the invention at various temperatures (determined at pH 5.5 with starch as substrate).

According to the invention, amylase is derived from an amylase producing strain of the genus Staphylothermus, in particular *Staphylothermus marinus*.

A strain representative of *Staphylothermus marinus* has been made publicly available under Accession No. DSM 3639. The number is published in the DSM Catalogue of Strains, 1993.

Production of Amylase

Amylase of the invention may be produced by anaerobic cultivation of the above mentioned strain on a nutrient medium containing suitable carbon and nitrogen sources, such media being known in the art. Anaerobic conditions may be achieved during the preparation of media by sparging with $N_2$ and following the anaerobic techniques as described by Balch and Wolfe in *Appl. Env. Microbiol.* 32, 1976, pp. 781–791.

Alternatively, amylase of the invention can be produced by aerobic cultivation of a transformed host organism containing the appropriate genetic information from the above mentioned strain. Such transformants can be prepared and cultivated by methods known in the art.

The amylase may be recovered by removing the cells from the fermentation medium (e.g. by centrifugation or filtration) and then concentrating the broth (e.g. by ultrafiltration). If desired, the amylase may be further purified by known methods.

Immunochemical Properties

The amylase of the invention has immunochemical properties identical or partially identical (i.e. at least partially identical) to those of an amylase derived from the strain *Staphylothermus marinus*, DSM 3639.

The immunochemical properties can be determined immunologically by cross-reaction identity tests. The identity tests can be performed by the well-known Ouchterlony double immunodiffusion procedure or by tandem crossed immunoelectrophoresis according to Axelsen N. H.; Handbook of Immunoprecipitation-in-Gel Techniques; Blackwell Scientific Publications (1983), chapters 5 and 14. The terms "antigenic identity" and "partial antigenic identity" are described in the same book, Chapters 5, 19 and 20.

Monospecific antisera are generated according to the above mentioned method by immunizing rabbits with the purified amylase of the invention. The immunogens are mixed with Freund's adjuvant and injected subcutaneously into rabbits every second week. Antisera are obtained after a total immunization period of 8 weeks, and immunoglobulins are prepared therefrom as described by Axelsen N. H., supra.

The Enzyme

An amylase of the invention can be characterized by having amylase activity at temperatures of from below 60° C. to above 120° C., having activity optimum at temperatures in the range 95°–105° C., determined at pH 5.5 with starch as substrate. The amylase can also be characterized by having amylase activity at pH values of from below pH 4.0 to above pH 10.0, having optimum in the range pH 4.5 to pH 5.5, determined at 95° C. with starch as substrate.

Determination of Amylase Activity

Amylase activity is determined by measuring the amount of reducing sugar released during the incubation with starch. One unit (U) of amylase activity is defined as the amount of amylase that releases 1 $\mu$mole of reducing sugar (as maltose standard) per min. under the following assay conditions: A 0.05 ml volume of 1% soluble starch is added to 0.05 ml of 0.1M sodium acetate buffer pH 5.5. 25 $\mu$l of enzyme solution are added to this mixture and the sample is incubated at 90° C. for 30 min. The reaction is stopped by cooling on ice, and the amount of reducing sugar is determined by dinitrosalicylic acid. Sample blanks are used to correct for nonenzymatic release of reducing sugar.

Industrial Applications

The amylase of this invention possess valuable properties allowing for various industrial applications. In particular the amylase, in being thermostable, finds potential application in the production of sweeteners and ethanol from starch. Conditions for conventional starch converting processes and liquefaction and/or saccharification processes are described in for instance U.S. Pat. No. 3,912,590 and EP patent publications Nos. 252,730 and 63,909.

The following example further illustrates the present invention, and it is not intended to be in any way limiting to the scope of the invention as claimed.

EXAMPLE 1

Cultivation

The strain *Staphylothermus marinus*, DSM 3639, was recultured from glycerol-preserved cells using the medium recommended by the Deutsche Sammlung von Mikroorganismen (DSM). The microorganisms were grown in 1 liter batch cultures under the following conditions: Medium: DSM377 (DSM377 is described in DSM Catalogue of Strains, 1993), pH 6.0, temp. 90° C.; in the medium sulphur and tryptone were omitted and starch (0.5% w/v) was added as the only carbohydrate; yeast extract concentration was 0.1% (w/v). The cell density achieved in this medium was $\geq 10^8$ cells/ml. Anaerobic conditions were achieved during the preparation of media by sparging with $N_2$ and following the techniques as described by Balch in *Appl. Env. Microbiol.* 32, 1976, pp. 781–791.

After cultivation the culture fluid was centrifuged at 12.000×g for 30 min. at 4° C., and the cell free supernatant was concentrated up to 100-fold using an Amicon Ultrafiltration System. The cell pellet was resuspended in 50 mM sodium acetate buffer pH 5.5 and sonicated three times for 3 min. at 50% duty cycle by a BRANSON 450 sonifier. The cell debris was separated from the supernatant after centrifugation at 10.000×g for 30 min. at 4° C.

The following total activity (U) in both supernatant and cell extract was found:

Amylase activity: 1.3 U/b 1

Temperature Optima

Temperature optima were determined by incubation of samples for 40 minutes at pH 5.5 at temperatures from 60° C. to 120° C. The incubation was conducted in closed Hungate tubes in order to prevent boiling of the solution.

FIG. 1 shows the result.

pH Optima

To determine pH optima, Universal buffer (Britten and Robinson) was used to obtain values from pH 4.0 to pH 10.0. Samples were incubated for 40 minutes at 95° C at the pH in question.

Figure 2:
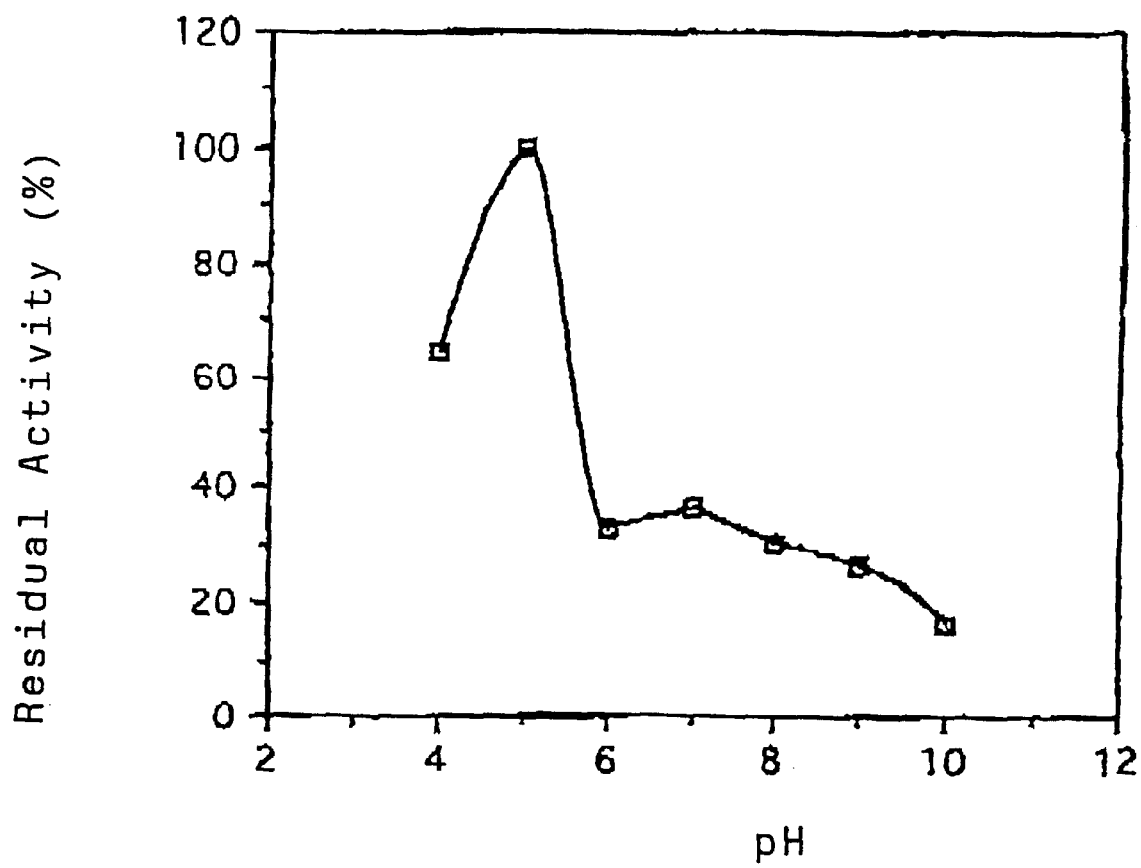
FIG. 2 shows the relative activity (% rel.) of an amylase ($\bowtie$) of the invention at various pH, determined at 95° C. with starch as substrate.

FIG. 2 shows the result.

We claim:

1. A purified amylase enzyme isolated from an amylase-producing strain of the genus Staphylothermus, having:

(a) an activity optimum in the range pH 4.5 to pH 5.5, determined at 95° C. with starch as substrate; and (b) an activity optimum at temperatures in the range 95°–105° C., determined at pH 5.5 with starch as substrate.

2. The purified amylase of claim 1, wherein the amylase-producing strain is *Staphylothermus marinus*.

3. The purified amylase of claim 2, wherein the amylase-producing strain is *Staphylothermus marinus*, DSM 3639.

4. A method of producing a sweetener from starch, comprising contacting starch with the amylase of claim 1, wherein a sweetener is produced; and recovering said sweetener.

5. The method of claim 4, wherein the amylase is obtained *Staphylothermus marinus*.

6. A method of producing ethanol from starch, comprising contacting starch with the amylase of claim 1, wherein a sweetener is produced; fermenting said sweetener to produce ethanol; and recovering said ethanol.

* * * * *